United States Patent [19]

Whaley et al.

[11] 4,293,651

[45] Oct. 6, 1981

[54] PROCESS FOR PRODUCING ANTIBIOTIC USING SACCHAROPOLYSPORA

[75] Inventors: Howard A. Whaley, Portage; John H. Coats, Kalamazoo, both of Mich.

[73] Assignee: The Upjohn Company, Kalamazoo, Mich.

[21] Appl. No.: 81,211

[22] Filed: Oct. 2, 1979

[51] Int. Cl.³ .............................................. C12P 1/06
[52] U.S. Cl. ................................... 435/169; 435/822
[58] Field of Search ........................................ 435/169

[56] References Cited

U.S. PATENT DOCUMENTS 4,148,883  4/1979  Celmet et al. ...................... 424/122

Primary Examiner—Alvin E. Tanenholtz
Attorney, Agent, or Firm—Roman Saliwanchik

[57] ABSTRACT

A process for preparing the antibiotic U-59,760. The process is a microbiological process using a biologically pure culture of the novel microbe *Saccharopolyspora hirsuta* strain 367, NRRL 12045. The antibiotic produced by the process is active against various microorganisms, for example, *Staphylococcus aureus*, *Streptococcus pyogenes*, and *Klebsiella pneumoniae*. Thus, antibiotic U-59,760 can be used in various environments to eradicate or control such bacteria.

2 Claims, No Drawings

PROCESS FOR PRODUCING ANTIBIOTIC USING SACCHAROPOLYSPORA

BRIEF SUMMARY OF THE INVENTION

The process of the invention utilizes the biologically pure culture of the novel microbe *Saccharopolyspora hirsuta* strain 367, NRRL 12045, to produce the useful antibiotic U-59,760. The physical and chemical characteristics of this antibiotic cannot be distinguished from the antibiotic known as compound 47444 which is disclosed in U.S. Pat. No. 4,148,883. The production of the antibiotic in U.S. Pat. No. 4,148,883 is accomplished by an entirely different microbe which is classified as a Nocardia.

DETAILED DESCRIPTION OF THE INVENTION

The microorganism used for the production of antibiotic U-59,760, as described herein, is a biologically pure culture of *Saccharopolyspora hirsuta* strain 367, NRRL 12045.

A subculture of this microorganism can be obtained from the permanent collection of the Northern Regional Research Laboratory, U.S. Department of Agriculture, Peoria, Illinois, U.S.A. Its accession number in this depository is NRRL 12045. It should be understood that the availability of the culture does not constitute a license to practice the subject invention in derogation of patent rights granted with the subject instrument by governmental action.

The microorganism of this invention was studied and characterized by Alma Dietz and Grace P. Li of The Upjohn Company Research Laboratories.

An actinomycete isolated in the Upjohn soils screening laboratory has been characterized and found to have the macroscopic, microscopic and whole cell hydrolysate properties of the genus Saccharopolyspora [Iwasaki, A., N. Itoh, and T. Mori, 1979. A new broadspectrum aminoglycoside antibiotic complex, sporaricin. II. Taxonomic studies on the sporaricin producing strain *Saccharopolyspora hirsuta* subsp. kobensis nov. subsp. J. Antibiotics, 32: 180-186.] [Lacey, J. and M. Goodfellow. 1975. A novel actinomycete from sugarcane bagasse: *Saccharopolyspora hirsuta* gen. et sp. novl. J. Gen. Microbiol. 88:75-87]. A comparison with the type culture *Saccharopolyspora hirsuta* ATCC 27875 is given in Tables 1 and 2. A comparison with the type culture and with the subspecies, *Saccharopolyspora hirsuta* ss. kobensis ATCC 20501 [Iwasaki, A. supra] based on data published for these strains is given in Table 3.

Unique properties of the genus Saccharopolyspora are its butyrous or gelatinous-type vegetative growth, sparse aerail growth which is best studied after 21 days incubation, yellow to orange to orange-tan vegetative growth and pigment production, spore chains developing in a sheath with unique hair tufts with truncated bases and smooth areas between the tufts, the presence of meso-diaminopimelic acid, arabinose and galactose in whole cell hydrolysates and in cell wall preparations. L-diaminopimelic acid was detected in addition to meso-DAP in our cell wall preparations.

No antibiotic production has been reported for the type culture; the subspecies kobensis produces the antibiotic complex sporaricin (KA-6606) [Iwasaki, A. supra]. The new isolate is distinguished by the production of antibiotic U-59,760 and U-59,761. The only significant difference among the strains is in their antibiotic production capability. Therefore, the new strain is designated *Saccharopolyspora hirsuta* strain 367.

The taxonomic methods used herein were those cited in Dietz [Dietz, A. 1954. Ektachrome transparencies as aids in actinomycete classification. Ann N. Y. Acad. Sci. 60: 152-154.] [Dietz, A. 1967. *Streptomyces steffisburgensis* sp. n. J. Bacteriol. 94: 2022-2026.], Dietz and Mathews [Dietz, A., and J. Mathews. 1971. Classification of Streptomyces spore surfaces into five groups. Appl. Microbiol. 21: 527-533.], Becker et al. [Becker, B., M. P. Lechevalier, and H. A. Lechevalier. 1966. Chemical composition of cell wall preparations from strains of various form-genera of aerobic actinomycetes. Appl. Microbiol. 13 236-243.], Lechevalier and Lechevalier [Lechevalier, H. A., and M. P. Lechevalier. 1970. A critical evaluation of the genera of aerobic actinomycetes, p. 393-405. In H. Prauser (ed.), The Actinomycetales. Gustav Fisher, Jena.] [Lechevalier, M. P., and H. A. Lechevalier. 1970. Chemical composition as a criterion in the classification of aerobic actinomycetes. Int. J. Syst. Bacteriol. 20: 435-443.], and Shirling and Gottlieb [Shirling, E. B., and D. Gottlieb. 1966. Methods for characterization of Streptomyces species. Int. J. Syst. Bacteriol. 16: 313-340.].

Color characteristics: Aerial mycelium gray to gray-pink (very sparse at 14 days). Melanin negative. Appearance on Ektachrome is given in Table 1. Surface colors of the vegetative growth were determined to be red (R) or yellow (Y) by matching the color with the chips in the Tresner and Backus [Tresner, H. D., and E. J. Backus. 1963. System of color wheels for streptomycete taxonomy. Appl. Microbiol. 11: 335-338.] color wheels.

Microscopic characteristics: Spore masses and spore chains, intact and fragmented, and flexuous or loosely spiraled chains, as observed by Scanning Electron Microscopy, appear to develop in a sheath which is at first almost smooth; then unique tufts of hairs (triangular at the base) are formed. The surface between the tufts is smooth. Finally, the sheath becomes covered with fine long hairs. The long sheaths are tangled and appear to arise from, or fuse to form pseudosporangia. As the chains come in contact with the substrate the spores become smooth in outline with a depressed or ridged appearance. "Empty" hyphae are noted in the developed chains. Microscopic characteristics are best noted after 21 days incubation at 28°-37° C. Nocardioform fragmentation may be seen in 21 day cultures.

Growth on carbon compounds: Under the test conditions of Shirling and Gottlieb [supra] growth was good on the positive control (basal medium plus D-glucose), sucrose, D-mannitol, D-fructose and raffinose. Growth was doubtful on L-arabinose and D-xylose. There was no growth on the negative control (basal medium only), inositol, rhamnose, and cellulose.

Whole cell analysis: meso-Diaminopimelic acid, arabinose and galactose were detected.

Cell wall analysis: meso-Diaminopimelic acid, L-diaminopimelic acid, arabinose and galactose were found.

Cultural and biochemical characteristics: See Table 2. Temperature: There was no to very poor growth at 18° C. on Bennett's and maltose-tryptone agars and poor growth on Czapek's sucrose agar. Growth was good at 24°-45° C. There was no growth at 55° C.

TABLE 1

Color characteristics* of *Saccharopolyspora hirsuta* ATCC 27875 and *S. hirsuta* strain 367 on Ektachrome

| Agar Medium | Determination | S. hirsuta ATCC 27875 Chip | Color | S. hirsuta strain 367 Chip | Color |
|---|---|---|---|---|---|
| Bennett's | S | 71 | moderate orange yellow | 71 | moderate orange yellow |
|  | R | 71 | moderate orange yellow | 71 | moderate orange yellow |
| Czapek's sucrose | S | 74 | strong yellowish brown | 67 | brilliant orange yellow |
|  | R | 72 | dark orange yellow | 67 | brilliant orange yellow |
| Maltose-tryptone | S | 71 | moderate orange yellow | 71 | moderate orange yellow |
|  | R | 71 | moderate orange yellow | 71 | yellow |
| Peptone-iron | S | 68 | strong orange yellow | 68 | strong orange yellow |
|  | R | 68 | strong orange yellow | 68 | strong orange yellow |
| 0.1% Tyrosine | S | 73 | pale orange yellow | 71 | moderate orange yellow |
|  | R | 73 | pale orange yellow | 71 | moderate orange yellow |
| Casein | S | 73 | pale orange yellow | 70 | light orange yellow |
|  | R | 73 | pale orange yellow | 73 | pale orange yellow |

*Color was determined by comparison with NBS color chips (SP 440. Color: Universal Language and Dictionary of Names. U.S. Government Printing Office, Washington, DC 20402. SRM 2106. ISCC-NBS Centroid Color Charts. Office of Standard Reference Material, Room B311, Chem. Building, National Bureau of Standards, Washington, DC 20234.
S = Surface
R = Reverse

TABLE 2

Cultural and biochemical characteristics of *Saccharopolyspora hirsuta* strains.

| Agar medium | Determination | S. hirsuta ATCC 27875 | S. hirsuta strain 367 |
|---|---|---|---|
| Peptone-iron | S | Colorless (V) | Colorless or light tan wrinkled (V) |
|  | R | Pale yellow | Orange-tan |
|  | P | — | Pale tan to orange-tan |
|  | O | Melanin negative | Melanin negative |
| Calcium malate | S | Trace-white (A) | Trace gray (A) |
|  | R | Cream | Pale gray cream |
|  | P | — | — |
|  | O | Malate solubilized | Malate slightly solubilized |
| Glucose asparagine | S | Colorless to light tan (V) | Light tan (V) |
|  | R | Orange | Orange-tan |
|  | P | Orange | Orange-tan |
| Skim milk | S | Tan (V) | Orange-brown (V) |
|  | R | Orange-tan | Dark orange-tan |
|  | P | Orange-tan | Deep orange-tan |
|  | O | Casein solubilized | Casein solubilized |
| Tyrosine | S | Tan (V) | Orange-tan (V) |
|  | R | Orange | Orange |
|  | P | Orange | Orange |
|  | O | Tyrosine solubilized | Tyrosine solubilized |
| Xanthine | S | Colorless (V) | Pale tan (V) |
|  | R | Pale yellow | Pale tan |
|  | P | Pale yellow | Pale tan-peach |
|  | O | Xanthine solubilized around growth | Xanthine solubilized |
| Nutrient starch | S | Colorless (V) | Pale tan (V) |
|  | R | Pale yellow | Pale tan |
|  | P | Very pale yellow | Very pale tan |
|  | O | Starch hydrolyzed | Starch hydrolyzed |
| Yeast extract-malt extract | S | Colorless (V) | Pale tan (V) |
|  | R | Orange | Pale orange-tan |
|  | P | Orange | Orange |
| Peptone-yeast extract-iron (ISP-6) | S | Colorless (V) with very slight trace white (A) | Colorless (V) |
|  | R | Yellow-tan | Light orange-tan to tan |
|  | O | Melanin negative | Melanin negative |
| Tyrosine (ISP-7) | S | Trace white (A) | Very pale orange (V) |
|  | R | Yellow tan | Very pale orange |
|  | O | Melanin negative | Melanin negative |
| Gelatin |  |  |  |
| Plain | S | Trace white (A) on colorless surface pellicle | Colorless to pale yellow (V) |
|  | P | None | None to trace pale yellow |
|  | O | Gelatin liquified | Gelatin liquified |
| Nutrient | S | Trace white (A) on yellow (V) pellicle | Trace colorless (V) to trace white (A) on (V) |
|  | P | None | None |
|  | O | Gelatin liquified | Gelatin liquified |
| Broth |  |  |  |
| Synthetic nitrate | S | No surface growth | Trace white (A) on colorless (V) |
|  | P | None | None |

TABLE 2-continued

Cultural and biochemical characteristics of *Saccharopolyspora hirsuta* strains.

| Agar medium | Determination | S. hirsuta ATCC 27875 | S. hirsuta strain 367 |
|---|---|---|---|
| | O | Compact bottom growth<br>No reduction | Compact to flocculent bottom growth<br>No reduction |
| Nutrient nitrate | S | Trace white (A) on colorless surface pellicle | Trace white (A) on colorless surface ring |
| | P | None | None |
| | O | Flocculent bottom growth; No reduction | Poor colorless compact bottom growth; No reduction |
| Litmus milk | S | Pale gray (A) on yellow-tan surface ring | Blue-gray surface ring |
| | P | None | Deep red-tan |
| | O | Litmus not reduced<br>pH 6.7-7.3 | Peptonization<br>pH 7.6-7.8 |

S = Surface
O = Other characteristics
R = Reverse
(V) = Vegetative Growth
P = Pigment
(A) = Aerial growth

TABLE 3

Comparison of *Saccharopolyspora hirsuta* strains

| Tests | S. hirsuta strain 367 | S. hirsuta ATCC 27875 | S. hirsuta kobense ATCC 20501 |
|---|---|---|---|
| Physiological Properties | | | |
| Temperature | Growth from 18-45C | Growth from 25-45C | Growth from 18-45C |
| Optimum Temperature | 28-45C | 37-40C | 37-42C |
| Gelatin liquefaction | Complete | Positive at 27C | Positive at 27C |
| Starch hydrolysis | Positive | Positive | Positive |
| Action on milk | No coagulation Peptonization | No coagulation Peptonization | No coagulation Peptonization |
| Melanoid pigment production | Negative | Negative | Negative |
| Nitrate reduction | Negative | Negative | Positive |
| Carnon Source Utilization | | | |
| L-Arabinose | ± | − | − |
| D-Xylose | ± | + | − |
| L-Rhamnose | − | + | − |
| D-Glucose | + | + | + |
| D-Fructose | ++ | + | + |
| Sucrose | + | + | + |
| Raffinose | ++ | + | + |
| Inositol | − | + | − |
| D-Mannitol | ++ | + | + |

The compound of the invention process is produced when the elaborating organism is grown in an aqueous nutrient medium under submerged aerobic conditions. It is to be understood, also, that for the preparation of limited amounts surface cultures and bottles can be employed. The organism is grown in a nutrient medium containing a carbon source, for example, an assimilable carbohydrate, and a nitrogen source, for example, an assimilable nitrogen compound or proteinaceous material. Preferred carbon sources include glucose, brown sugar, sucrose, glycerol, starch, cornstarch, lactose, dextrin, molasses, and the like. Preferred nitrogen sources include cornsteep liquor, yeast, autolyzed brewer's yeast with milk solids, soybean meal, cottonseed meal, cornmeal, milk solids, pancreatic digest of casein, fish meal, distiller's solids, animal peptone liquors, meat and bone scraps, and the like. Combinations of these carbon and nitrogen sources can be used advantageously. Trace metals, for example, zinc, magnesium, manganese, cobalt, iron, and the like, need not be added to the fermentation media since tap water and unpurified ingredients are used as components of the medium prior to sterilization of the medium.

Production of the compound by the invention process can be effected at any temperature conducive to satisfactory growth of the microorganism, for example, between about 18° and 40° C., and preferably between about 20° and 28° C. Ordinarily, optimum production of the compound is obtained in about 3 to 15 days. The final pH of the fermentation is dependent, in part, on the buffers present, if any, and in part on the initial pH of the culture medium.

When growth is carried out in large vessels and tanks, it is preferable to use the vegetative form, rather than the spore form, of the microorganism for inoculation to avoid a pronounced lag in the production of the compound and the attendant inefficient utilization of the equipment. Accordingly, it is desirable to produce a vegetative inoculum in a nutrient broth culture by inoculating this broth culture with an aliquot from a soil, liquid $N_2$ agar plug, or a slant culture. When a young, active vegetative inoculum has thus been secured, it is transferred aseptically to large vessels or tanks. The medium in which the vegetative inoculum is produced can be the same as, or different from, that utilized for the production of the compound, so long as a good growth of the microorganism is obtained.

A variety of procedures can be employed in the isolation and purification of the compound produced by the subject invention from fermentation beers. Isolation can be accomplished by extraction with solvents such as methylene chloride, acetone, butanol, ethyl acetate and the like; and silica gel chromatography can be used to purify crude preparations of the antibiotic.

In a preferred recovery process, the compound produced by the subject process is recovered from the culture medium by separation of mycelia and undissolved solids by conventional means, such as by filtration or centrifugation, and solvent extraction of both mycelial cake or clarified broth. The clarified broth can be extracted with a suitable solvent, for example, methylene chloride (preferred), ethylacetate, butanol, and MIBK. The extract can be evaporated under reduced pressure to a concentrate and the antibiotic recovered from this concentrate by subjecting the concentrate to chromatography over silica gel and eluting with methanol and methylene chloride.

The following examples are illustrative of the process of the invention, but are not to be construed as limiting. All percentages are by weight and all solvent mixture proportions are by volume unless otherwise noted.

EXAMPLE 1

Part A. Fermentation

A biologically pure culture Saccharopolyspora hirsuta strain 367, NRRL 12045, is used to inoculate 500-ml Erlenmeyer seed flasks containing 100 ml of sterile medium consisting of the following ingredients:

| | | |
|---|---|---|
| Glucose monohydrate | 25 g/l | |
| Pharmamedia* | 25 g/l | |
| Tap water q.s. | 1 liter | |

*Pharmamedia is an industrial grade of cottonseed flour produced by Traders Oil Mill Company, Fort Worth, Texas.

The seed medium presterilization pH is 7.2. The seed inoculum is grown for three days at 28° C. on a Gump rotary shaker operating at 250 rpm and having a 2½ inch stroke.

After three days incubation, the seed medium is used to inoculate (the inoculation rate is 5 ml of seed inoculum per 100 ml of fermentation medium) a series of 500-ml Erlenmeyer flasks containing sterile fermentation medium consisting of the following ingredients:

| | | |
|---|---|---|
| Glucose monohydrate | 10 g/l | |
| Dextrin | 20 g/l | |
| Corn steep liquor | 2.5 g/l | |
| $NH_4NO_3$ | 3.0 g/l | |
| NaCl | 2.0 g/l | |
| $CaCO_3$ | 5.0 g/l | |
| pH-7.2 (presterilization) | | |

The fermentation flasks are incubated at a temperature of 28° C. on a Gump torary shaker operating at 250 rpm and having a 2½ inch stroke. Harvest is usually after about 5 days of fermentation. A typical 5 day fermentation has the following titers of antibiotic in the fermentation broth:

| Day | S. lutea Assay, Bu/ml |
|---|---|
| 2 | 8.0 |
| 3 | 10.4 |
| 4 | 10.4 |
| 5 | 11.2 |

In the assay results, a biounit (BU) is defined as the concentration of the antibiotic which gives a 20 mm zone of inhibition under the standard assay condition. Thus, if, for example, a fermentation beer has to be diluted 1/100 to give a 20 mm zone of inhibition, the potency of such beer is 100 Bu/ml.

B. Recovery and Purification

The whole beer (ca. 5,000 l) from a fermentation, as described above, is adjusted to pH 7.3 with NaOH and filtered on a 30 inch filter press using diatomaceous earth as a filter aid. During the filtration operation wash water is applied to the filter cake. From the filtration operation is recovered 5,500 l of clear fermentation broth which is then extracted twice with methylene chloride (1,400 l each time) to give a total of 2.800 l of solvent extract. This solvent extract is concentrated in vacuo to 10 l. Assay on a standard S. lutea disc plate assay gives a value of 2424 Bu/ml.

The extract concentrate described above (9 l), is chromatographed over a column containing 9 kg of silica gel (E. Merck-silica gel 7734). The column is eluted as follows:

20 liters methylene chloride; then 40 liters 2% methanol in methylene chloride; then 150 liters 5% methanol in methylene chloride; then 100 liters 10% methanol in methylene chloride. Four liter fractions are collected after an 80 liter forerun. Fractions 5–8 contain antibiotic U-59,760 having the following characteristics:

Elemental Analysis: C, 64.95, H, 7.42, N, 2.49

Molecular Weight: 515.2482 (Mass spectroscopy) ($C_{28}H_{37}NO_8$).

Optical Rotation: $[\alpha]_D^{25} +53°$ (C, 0.0848 MeOH).

Solubilities: Soluble in methanol, ethanol and methylene chloride, and relatively insoluble in petroleum ether and cyclohexane.

Infrared Absorption Spectrum: Antibiotic U-59,670 has a characteristic infrared absorption spectrum in a mineral oil mull. Peaks are observed at the following wave lengths expressed in reciprocal centimeters.

| Band Frequency (Wave Numbers) | Intensity |
|---|---|
| 3459 | S |
| 3330 | S, sh. |
| 3139 | M, sh. |
| 3025 | M |
| 2957 | S |
| 2922 | S |
| 2855 | S |
| 2725 | W |
| 1725 | S, sh. |
| 1704 | S |
| 1688 | S |
| 1554 | M |
| 1455 | S |
| 1411 | S |
| 1377 | S |
| 1354 | S |
| 1339 | S |
| 1315 | S, sh. |
| 1307 | S |
| 1276 | S |
| 1265 | S, sh. |
| 1240 | S |
| 1205 | M |
| 1169 | S |
| 1109 | S |
| 1082 | S |
| 1060 | S |
| 1045 | S |
| 1031 | S |
| 1010 | S |
| 968 | S |

| Band Frequency (Wave Numbers) | Intensity |
|---|---|
| 956 | S |
| 949 | S |
| 937 | M |
| 909 | M |
| 882 | M |
| 870 | M, sh. |
| 857 | M |
| 835 | M |
| 794 | M |
| 764 | S |
| 747 | S |
| 719 | M |
| 699 | M |
| 677 | M |
| 638 | M |

Key:
S = Strong,
M = Medium,
W = Weak,
sh. = shoulder

| Antimicrobial spectrum: Organism | Inhibition Zone Size (mm)[1] |
|---|---|
| B. subtilis UC 564 | 0 |
| B. subtilis UC 6033 | 16 |
| S. aureus UC 70 | 36 |
| S. aureus UC 3665 | 42 |
| S. aureus UC 6029 | 38 |
| S. lutea UC 130 | 42 |
| S. lutea UC 3383 | 41 |
| S. lutea sens | 45 |
| K. pneumoniae UC 58 | 32 |
| E. coli UC 51 | 0 |
| S. schottmuelleri UC 126 | 0 |
| P. vulgaris UC 93 | 0 |
| P. aeruginosa UC 95 | 0 |
| M. avium UC 159 | 30 |
| P. oxalicum UC 1268 | 0 |
| S. pastorianus UC 1342 | 0 |
| R. sphaeroides UC 3238 | 21 |
| S. pyogenes UC 6055 | 16 |
| B. fragilis UC 6513 | 37 |
| C. perfringens UC 6509 | 48 |

"UC" is a registered trademark of The Upjohn Company culture collection. These cultures can be obtained from The Upjohn Company in Kalamazoo, Michigan, upon request.

Since antibiotic U-59,760 is active against *S. aureus*, it can be used to disinfect washed and stacked food utensils contaminated with this bacteria. Also, it can be used as a disinfectant on various dental and medical equipment contaminated with *S. aureus*. Further, antibiotic U-59,760 can be used as a bacteriostatic rinse for laundered clothes, and for impregnating papers and fabrics; and, it is also useful for suppressing the growth of sensitive organisms in plate assays, and other microbiological media.

We claim:

1. A process for preparing antibiotic U-59,760, which comprises cultivating *Saccharopolyspora hirsuta* strain 367, having the identifying characteristic of NRRL 12045, in an aqueous nutrient medium under aerobic conditions until substantial antibiotic U-59,760 activity is imparted to said medium and separating antibiotic U-59,760 from said medium.

2. A process, according to claim 1, wherein said aqueous nutrient medium contains a source of assimilable carbohydrate and assimilable nitrogen.

* * * * *